(12) United States Patent
Arseguel et al.

(10) Patent No.: US 6,652,844 B1
(45) Date of Patent: Nov. 25, 2003

(54) SOLID PRODUCT CAPABLE OF BEING HANDLED BASED ON HYDROPHOBIC MINERAL POWDER

(75) Inventors: Didier Arseguel, Deyme (FR); Pierre Charles Goffinet, Gif sur Yvette (FR); Brigitte Riviere, Poitiers (FR)

(73) Assignee: Talc de Luzenac, Luzenac (FR)

( * ) Notice: Subject to any disclaimer, the term of this patent is extended or adjusted under 35 U.S.C. 154(b) by 0 days.

(21) Appl. No.: 09/719,470
(22) PCT Filed: Jun. 21, 1999
(86) PCT No.: PCT/FR99/01481
§ 371 (c)(1), (2), (4) Date: Dec. 13, 2000
(87) PCT Pub. No.: WO99/66885
PCT Pub. Date: Dec. 29, 1999

(30) Foreign Application Priority Data

Jun. 23, 1998 (FR) .............................................. 98 07936
Oct. 1, 1998 (FR) .............................................. 98 12307

(51) Int. Cl.⁷ .............................................. A61K 7/035
(52) U.S. Cl. .......................................... 424/69; 424/63
(58) Field of Search ..................................... 424/69, 63

(56) References Cited

U.S. PATENT DOCUMENTS

| | | | |
|---|---|---|---|
| 4,783,333 A | * 11/1988 | Mercado et al. | ............... 424/63 |
| 4,804,538 A | 2/1989 | Chen | |
| 4,837,011 A | 6/1989 | Macchio et al. | |
| 5,023,075 A | 6/1991 | Macchio et al. | |
| 5,849,333 A | * 12/1998 | Nordhauser et al. | ......... 106/626 |
| 6,001,341 A | * 12/1999 | Genova et al. | ............. 424/401 |

FOREIGN PATENT DOCUMENTS

| | | |
|---|---|---|
| EP | 0 587 415 | 3/1994 |
| WO | WO 96/30448 | 10/1996 |
| WO | WO 97/04737 | 2/1997 |
| WO | WO 98/30195 | 7/1998 |

OTHER PUBLICATIONS

Handbook of Cosmetic Science and Technology, 1st Edition, 1993, pp. 134–145.
Cosmetics & Toiletries, vol. 107, Apr. 1992 pp. 95 and 96.

* cited by examiner

Primary Examiner—Thurman K. Page
Assistant Examiner—Robert M. Joynes
(74) Attorney, Agent, or Firm—Young & Thompson

(57) ABSTRACT

The invention relates to a method of making a solid product in a form capable of being handled based on hydrophobic mineral powder such as talcum or mica powder, in particular for cosmetic or hygienic use. This process is characterized in that a hydrophobic mineral powder, particularly based on talcum or mica, is impregnated using a volatile liquid binder in proportions by weight such that the proportion of volatile liquid binder is at least equal to 5% and the proportion of mineral powder at least equal to 80%, and in that the resulting impregnated powder is pressed so as to shape it and to provide it with cohesion ensuring the rigidity of the product. The solid product obtained can take the form of a stick (7) that can be used to ensure a deposit of talcum or mica by contact.

15 Claims, 1 Drawing Sheet

SOLID PRODUCT CAPABLE OF BEING HANDLED BASED ON HYDROPHOBIC MINERAL POWDER

The invention relates to a solid product based on hydrophobic mineral powder, particularly talcum or mica, having a predetermined characteristic shape that lends itself to handling, especially in the form of a stick. In particular, it concerns a solid product for cosmetic or hygienic use, enabling talcum or mica to be deposited on the skin by contact and gentle rubbing. The invention also relates to a manufacturing method enabling such a product to be obtained with a rigidity and cohesion compatible with its being used without risk of breaking or crumbling.

Talcum is often used in the form of a powder as an active ingredient in cosmetics owing to its emollient properties. The deposit of talcum or the thin film formed protects the skin from redness and irritation, protects the epidermis from rubbing and absorbs excess perspiration. This very old application is carried out by dusting powder on to the surface to be treated and, in practice, is somewhat inconvenient: dusting creates a cloud of powder of greater or lesser size, depending on how fine the talcum is, which pollutes the atmosphere, soils surfaces other than the surface to be treated and leads to material losses.

Furthermore, talcum or mica powder is incorporated in numerous cosmetic formulations as a filler. This mineral powder is generally pressed with active ingredients and fatty binders of the paraffin, lanolin, glycerin or stearate types to obtain a friable paste, which is placed in a pot or tub, generally to be applied using a brush (particularly where make-up products are concerned). In these products, the talcum or mica acts as a filler, which is essentially used to dilute the active ingredient or ingredients into which it is incorporated. This paste contained in the pot or tub has no inherent strength, but, taking into account its packaging, weak cohesion and high friability are acceptable, which enables proportions of talcum or mica of the order of 40 to 50% to be provided, exceptionally reaching 80% in certain products (WO 97/04737 relating to a composition "with high levels of talcum"; "Handbook of Cosmetic Science and Technology"; $1^{st}$ edition, 1993, p. 134–145, U.S. Pat. No. 4,837,011, EP 0 587 415, WO 98.30195). A high proportion of talcum or mica combined with a relatively low proportion of fatty binder limit the "greasy" effect created by the product when it is applied.

Furthermore, sticks exist for lips (lipsticks or coating sticks) comprising active ingredients and fatty binders, which enable a finishing or protective fatty layer to be deposited on the lips. These sticks have sufficient strength to enable them to be handled but do not generally contain talcum or mica (which are known to have unfavorable effects on particle cohesion). The "Handbook of Cosmetic Science and Technology" cited above provides the most common formulations of this type of sticks (p. 147–155). However, it should be noted that the journal "Cosmetics and Toiletries, April 1992" gives, on p. 95 and 96, a formulation for a stick for lips containing a small percentage of mica (5%) or talcum (3.65%).

Mineral powders of talcum or mica, and hydrophobic mineral powders more generally, are therefore known to agglomerate with difficulty and to give very friable cakes as soon as the proportion of mineral powder in the product becomes high; this explains why, for more than a century, talcum has been used in the form of a powder when it is intended to be applied alone (or in by far the greatest proportion) as an active cosmetic or hygienic ingredient. For several decades, the development of the numerous formulations referred to above, including talcum or mica as a filler, have only confirmed this teaching, since products with a high load of talcum or mica are products without any inherent cohesion, necessarily contained in pots, tubs or other containers to be applied using an instrument such as a brush, and the very rare stick products containing talcum include very little of it.

It can be noted that certain documents propose the coating of particles of hydrophobic powder to modify their surface properties (U.S. Pat. No. 5,023,075, WO 96.30448); however, it does not appear that the object of this treatment is to make solid products; at any rate, such techniques do not constitute a solution to the problem of the invention, since the characteristics of the initial natural powder are modified.

The present invention proposes the provision of a solid product based on hydrophobic mineral powder, such as talcum or mica, having a rigid shape that enables it to be handled so that a mineral compound can be applied directly by contact with the surface to be treated: the invention aims to avoid in this way the disadvanitages associated with the treatments mentioned above by the dusting of powder.

The object of the invention is in particular to provide a product in the form of a stick or other shape capable of being handled, which is essentially made up of a mineral powder based on talcum or mica (i.e. in which the other components represent less than 20 wt. % of the product) and which benefits from the following features:

inherent cohesion and strength compatible with use by contact without the solid product breaking or crumbling, good distribution of talcum or mica by contact with the surface to be treated, dry impression on application, with no greasy effect.

Another object of the invention is to avoid the so-called "polishing" effect, which consists in a reduction in the distribution after several applications.

To this end, the method according to the invention for making such a solid product with a characteristic shape and cohesion making it capable of being handled is characterized in that the hydrophobic mineral powder, particularly mineral powder based on talcum or mica, is impregnated using a volatile liquid binder in proportions by weight such that the proportion of volatile liquid binder is at least equal to 5% and the proportion of mineral powder at least equal to 80%, and in that the resulting impregnated powder is pressed so as to shape it and provide it with cohesion ensuring the rigidity of the product.

"Mineral powder based on talcum or mica" means a powder in which talcum or mica, or a mixture of the two, represents at least 75 wt. % of the powder (generally more than 85%, preferably more than 95%, or even 100%), any other components being mineral components such as kaolin, carbonate etc., or possibly organic, such as starch etc. "Talcum" means either the mineral hydrous magnesium silicate or the mineral chlorite (hydrous magnesium and aluminum silicate), or a mixture of the two. "Mica" means aluminous micas such as sericite, muscovite, magnesium micas such as phlogopite, and aluminous or magnesium illites derived from the above minerals by variable substitutions of Al for Si on the one hand, and of Fe for Al or Mg on the other hand.

"Volatile liquid binder" means a binder that is liquid at normal temperature and pressure having a volatility, defined by DIN standard 53249, such that the loss of weight is greater than or equal to 30% after 100 minutes at 25° C. This type of volatile binder always has a viscosity of less than 50 centipoises.

The term "press" means any operation for compressing grains of powder, particularly the operation of pressing in any press system, extrusion operation etc., the resulting solid product then being removed from the press to be packaged according to its shape and the intended application.

Tests have shown that it was possible to make, using the method of the invention, products based on hydrophobic mineral powder, such as talcum or mica powder, having rigidity and cohesion compatible with good shape stability and handling without breaking or crumbling (during manufacture when removing from the mold and during use), while giving a dry impression when applied to the skin (no "greasy" effect): talcum can thus be used by contact to serve as an active ingredient under the same conditions as traditional talcum powder products capable of being dusted. On contact with the surface to be treated, the product separates on the surface leading to good distribution of the mineral compound and a deposit or film suitable for achieving the desired treatment. No polishing effect is observed, even after a large number of applications (unless the pressing pressures are very high).

The optimum pressing pressures for the impregnated powder depend on the mineral powder and the volatile liquid binder used and on the proportion thereof (and any additives); a pressure of between 200 and 700 kg/cm$^2$ generally gives good results for talcum and mica powders. The impregnated powder is placed in a mold, the shape of which is adapted to the desired shape, and the above pressure is applied in particular using a piston (with evacuation of air).

The shape given to the product during pressing is preferably that of a stick, but may be different, depending on the application: cake, cylinder etc.

The volatile liquid binder used is advantageously a cyclic liquid silicone, particularly from the family of the cyclomethicones with a low degree of polymerization such that its viscosity is less than 10 centipoises, and preferably less than or equal to 5 centipoises. These compounds lead to a product of excellent quality (inherent strength/distribution/dry impression/lack of polishing effect).

It is possible to add to the product a small percentage of organic fatty binder in powder form, particularly the powder of a metal stearate. This addition increases the quality of distribution of the product by contact but also increases the "greasy" effect and the friability. It has been observed that a weight proportion of fatty binder lower than the proportion of volatile liquid binder led to good results; an excellent compromise consists in adding to the hydrophobic mineral powder approximately between 6 wt. % and 9 wt. % of volatile liquid binder and between 2 wt. % and 3 wt. % of metal stearate powder. It should be noted that the products formed with these proportions of fatty binder but in the absence of volatile liquid binder (or with a reduced proportion lower than that of the fatty binder) have very marked friability incompatible with obtaining a stable shape capable of being handled (in the case of a complete absence of volatile liquid binder, a large number of products break when being removed from the mold).

Other additives, such as perfume or emollient, can also be added to the powder in small proportions (i.e. less than or equal to 2%).

The invention also relates to the novel product constituted by a solid shape capable of being handled, particularly a stick, suitable for creating a deposit of mineral compound, such as talcum or mica, by contact, said product comprising a pressed hydrophobic mineral powder impregnated with a volatile liquid binder, the mineral powder representing between 80% and 95% of the total weight and the volatile liquid binder at least 5% of the said weight. The mineral powder is particularly a powder based on talcum or mica because of the cosmetic or hygienic properties of these compounds. In the case of talcum, it is thus possible to make a stick containing, as solids, at least 95% talcum, particularly 100% (weight of talcum in relation to the weight of solids in the product).

The following examples illustrate the implementation of the method of the invention and the characteristics of the resulting products. All the examples and the comparative tests were implemented using a pressing device as represented in the drawing: in this drawing.

Figure 1:
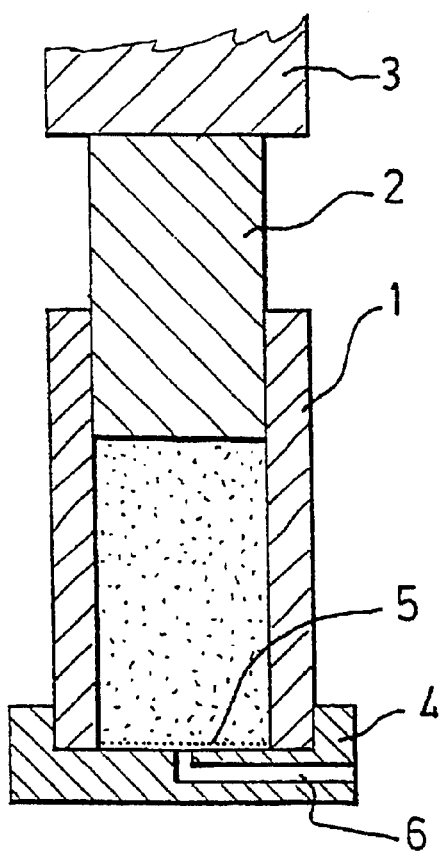
FIG. 1 is a diagrammatic cross section of the said pressing device.

The pressing device comprises a cylinder 1, having a compression chamber acting as a mold, into which a piston 2, connected to an upper platen 3, is able to penetrate. The cylinder 1 rests on a removable support 4, which seals it off at the lower part and is provided with a sintered disc 5 and an air evacuation duct 6. After the pass, the resulting product is removed from the mold and packaged using a support or packaging adapted to its shape, enabling it to be grasped.

Figure 2:
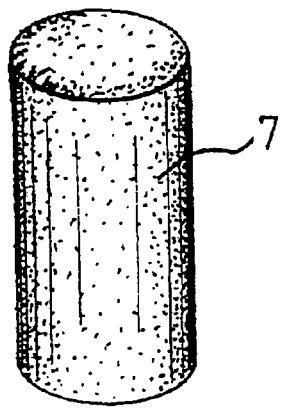
FIG. 2 is a diagram of the stick produced.

The sticks made in the examples are cylindrical in shape, like the stick 7 shown as a diagram in FIG. 2, with a diameter equal to 37 mm and a height equal to 50 mm.

EXAMPLE 1

In this example, talcum having a grain size distribution characterized by a diameter $D_{50}$ of 15 microns, a diameter $D_{95}$ of 40 microns and a cut diameter $D_{99}$ of 75 microns is used ("average diameter $D_{50}$ or diameter $D_{95}$" means a particle diameter such that 50% or 95% respectively of the particles are of a size smaller than this value; "cut diameter $D_{99}$" means a particle diameter such that less than 1% of the particles have a size greater than this value).

This talcum contains 94.5% hydrous magnesium silicate, 3% chlorite (hydrous magnesium and aluminum silicate) and 1.5% calcium carbonate. The non-compacted apparent density of the powder is 0.43 g/cm$^3$.

This talcum powder is mixed with a magnesium stearate powder having similar granulometry to that of the talcum. The whole mixture is gradually impregnated with cyclomethicone pentamer, which is a volatile liquid cyclic compound at ambient temperature and pressure (volatility of 84% according to the definition given on page 4). The impregnated powder is then homogenized.

The resulting impregnated powder has the following composition by weight: 90% talcum, 7.5% volatile liquid binder and 2.5% stearate.

A mass of 115 g of impregnated powder is placed into the cylinder 1 and a pressure of 500 kg/m$^2$ is applied by means of the piston 2. The whole mixture is held under the press for approximately 15 minutes.

The resulting product is removed from the mold by withdrawing the removable base 4. A cylindrical stick is obtained as shown in FIG. 2, having good strength and inherent cohesion, without a tendency to crumble or break.

Figure 3:
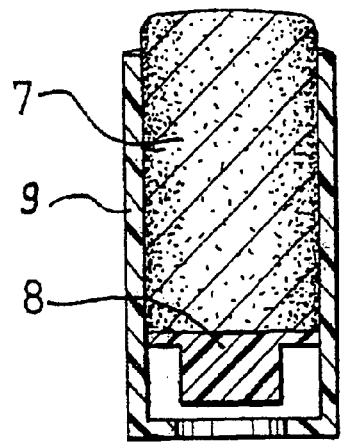
FIG. 3 is a diagram of a cross section of the stick in packaging facilitating its use.

This stick can be placed in classical packaging 9, comprising a pushing device 8 to enable the end of the stick to be pushed out as it is used up (FIG. 3).

This stick is subjected to qualitative tests to evaluate the following parameters: friability, talcum distribution, polishing and feel.

Polishing is evaluated by the distribution obtained after 10 applications. Several assessments are given:

F=friability: very friable, average, slight, zero
D=distribution: very good, good, average, zero
P=polishing: marked, slight, very slight, zero
F=feel: dry, slightly greasy, greasy, very greasy A talcum-based hygiene product in stick form can be considered satisfactory if its friability is slight or zero, its distribution very good, good or average, its polishing zero or very slight and its touch dry (or possibly slightly greasy). The following table gives the characteristics of the product made in this example.

| F | D | P | F |
|---|---|---|---|
| zero | good | zero | dry |

This product is satisfactory. It does not crumble or break. It gives a correct distribution of talcum even after several applications, and its feel is equivalent to that of a dusting of talcum powder.

EXAMPLE 2

This example reproduces the method of example 1 with a different composition of the impregnated powder:
90% talcum
10% cyclomethicone pentamer
The results obtained are as follows:

| F | D | P | F |
|---|---|---|---|
| zero | average | zero | dry |

This product is also suitable. The distribution is slightly less good.

EXAMPLE 3

Same conditions for the method but with a smaller proportion of volatile liquid binder:
95% talcum
5% cyclomethicone pentamer
The results obtained are as follows:

| F | D | P | F |
|---|---|---|---|
| slight | good | zero | dry |

This product remains satisfactory but its friability is greater than that of those of examples 1 and 2 and a smaller proportion of volatile liquid binder would entail risks of crumbling or breaking (as demonstrated by the comparative tests in the absence of binder).

EXAMPLE 4

This example is implemented under the same conditions as before, with an impregnated powder composed of:
90% talcum
7.5% cyclomethicone tetramer (volatility 100% according to the definition given above)
2.5% magnesium stearate.

The results obtained are as follows:

| F | D | P | F |
|---|---|---|---|
| slight | average | zero | dry |

This product is satisfactory.

EXAMPLE 5

A product is made in the same way with the following formulation:
89.8% talcum
7.5% cyclomethicone pentamer
2.5% magnesium stearate
0.12% perfume (ref. "PE8034")
0.025 ethanol.

The perfume reference "PE 8034" ("Douceur coton" from Quest) is solubilised in the ethanol and added after the volatile liquid binder.

The results are the same as in example 1.

cl EXAMPLE 6

In this product the proportion of volatile binder and that of the magnesium stearate are increased.
85% talcum
7.5% cyclomethicone tetramer
7.5% magnesium stearate
The results obtained are as follows:

| F | D | P | F |
|---|---|---|---|
| slight | average | zero | slightly greasy |

This product gives a feel with a slight impression of fat, which may rule it out in certain applications (particularly if the desired impression is identical to that of a dusted talcum powder).

Comparative Test (Talcum Only)

In this test, the pressing process is employed using a powder consisting only of talcum, and it is pressed on the one hand at 500 kg/cm², as before, and on the other hand at 1000 kg/cm In both cases, the powder crumbles as soon as it is removed from the mold, without the formation of a stick being possible.

Comparative Test (Talcum and Stearate)

In this test, the process is employed with a mixture of powder having the following composition:
90% talcum
10% magnesium stearate
The stick breaks when removed from the mold and a piece of stick undergoes the evaluation tests:

| F | D | P | F |
|---|---|---|---|
| very friable | very good | zero | greasy |

This product cannot be used in stick form, on the one hand for reasons of strength and cohesion (production and use), and on the other hand for its feel, which is too greasy (an impression far from the dry feel of a dusted talcum powder).

Comparative Test (Talcum, Stearate, Small Proportion of Volatile Binder)

In this test, the process is employed with a composition as follows:

90% talcum 7.5% magnesium stearate 2.5% cyclomethicone tetramer

The product is removed from the mold satisfactorily, without breaking. The test results are as follows:

| F | D | P | F |
|---|---|---|---|
| very friable | good | zero | slightly greasy |

The product is much too friable to allow it to be used as a stick.

EXAMPLE 7

In this example, mica of the sericite type is used, having a grain size distribution characterized by a diameter $D_{50}$ of 3.3 microns and a cut diameter $D_{99}$ of 15 microns.

This mica powder is mixed with a magnesium stearate powder. The whole mixture is gradually impregnated with cyclomethicone pentamer (volatility of 84% according to the definition given on page 4). The impregnated powder is then homogenized.

The resulting impregnated powder has the following composition by weight: 85% mica, 11% volatile liquid binder and 4% stearate.

A mass of 135 g of impregnated powder is placed into the cylinder 1 and a pressure of 500 kg/m² is applied by means of the piston 2. The whole mixture is held under the press for approximately 15 minutes.

The resulting product is removed from the mold by withdrawing the removable base 4. A cylindrical stick is obtained, having good strength and inherent cohesion, without a tendency to crumble or break.

This stick is subjected to qualitative tests to evaluate the following parameters: friability, mica distribution, polishing and feel. The assessment is performed exactly as in example 1.

The following table gives the characteristics of the product made in this example.

| F | D | P | F |
|---|---|---|---|
| zero | good | zero | dry |

This product is satisfactory. It does not crumble or break. It gives a correct distribution of mica even after several applications, and its feel is equivalent to that of a deposit using a brush.

Comparative Test (Mica Only)

In this test, the pressing process is employed using a powder consisting only of mica of the sericite type, identical to that used in example 7, and it is pressed at 500 kg/cm².

The powder is extremely friable and crumbles partially when removed from the mold; the imperfect stick formed loses its cohesion on use and does not possess the stability necessary for normal repeated application.

What is claimed is:

1. A stick, suitable for creating a mineral deposit by contact, comprising a powder containing at least 75% by weight of bare particles of hydrophobic mineral compounds, pressed and impregnated with a volatile liquid binder, said powder representing, at the end of manufacturing, between 80 wt. % and 95 wt. % talcum or mica and at least 5 wt. % volatile liquid binder.

2. A stick as claimed in claim 1, wherein the volatile liquid binder is a cyclic silicone with a viscosity less than or equal to 10 centipoises.

3. A stick as claimed in claim 1, comprising a proportion of organic fatty binder which is less than the proportion of volatile liquid binder.

4. A stick as claimed in claim 3, comprising approximately between 6 wt. % and 9 wt. % volatile liquid binder and between 2 wt. % and 3 wt. % metal stearate.

5. A stick as claimed in claim 1, wherein the volatile liquid binder is cyclomethicone.

6. A stick as claimed in claim 1, wherein the organic fatty binder is a metal stearate.

7. A stick as claimed in claim 1, further comprising perfume or emollient incorporated in the powder in a proportion by weight of less than or equal to 2%.

8. A stick, suitable for creating a mineral deposit by contact, comprising a powder containing at least 75% by weight of bare particles of hydrophobic mineral compounds, pressed and impregnated with a volatile liquid binder, said powder containing, as salts, at least 95% talcum by weight, wherein said weight of talcum is in relation to the weight of solids in the stick.

9. A stick as claimed in claim 8, wherein the volatile liquid binder is a cyclic silicone with a viscosity less than or equal to 10 centipoises.

10. A stick as claimed in claim 8, comprising a proportion of organic fatty binder which is less than the proportion of volatile liquid binder.

11. A stick as claimed in claim 8, wherein the volatile liquid binder is cyclomethicone.

12. A stick as claimed in claim 10, wherein the organic fatty binder is a metal stearate.

13. A stick as claimed in claim 8, wherein perfume or emollient is incorporated in the powder in a proportion by weight of less than or equal to 2%.

14. A method of making a solid stick product in a form capable of being handled based on hydrophobic mineral compounds, for topical application, wherein the powder containing at least 75% by weight of bare particles of hydrophobic mineral compounds is impregnated using a volatile liquid binder in proportions by weight such that between 80 wt. % and 95 wt. % talcum or mica and at least 5 wt. % volatile liquid binder are present, and wherein the resulting impregnated powder is pressed so as to shape it and to provide it with cohesion ensuring the rigidity of the product.

15. A method as claimed in claim 14, wherein perfume or emollient is incorporated in the powder in a proportion by weight of less than or equal to 2%.

* * * * *